United States Patent
Newton et al.

(10) Patent No.: US 11,827,907 B2
(45) Date of Patent: Nov. 28, 2023

(54) METHOD FOR INFECTING CELLS WITH VIRUS

(71) Applicant: Resilience Government Services, Inc., San Diego, CA (US)

(72) Inventors: Perry Newton, Alachua, FL (US); Dalton Berrie, Newberry, FL (US); Tyler Grow, Alachua, FL (US); Sheldon Doxilly, Alachua, FL (US); Christopher J. Montoya, Alachua, FL (US); Sara Jane Terpening, Frederick, MD (US); Eric Vela, Bell, FL (US)

(73) Assignee: RESILIENCE GOVERNMENT SERVICES, INC., San Diego, CA (US)

( * ) Notice: Subject to any disclaimer, the term of this patent is extended or adjusted under 35 U.S.C. 154(b) by 0 days.

(21) Appl. No.: 17/748,664

(22) Filed: May 19, 2022

(65) Prior Publication Data
US 2023/0002739 A1 Jan. 5, 2023

Related U.S. Application Data

(63) Continuation of application No. PCT/US2021/056381, filed on Oct. 23, 2021.

(60) Provisional application No. 63/104,803, filed on Oct. 23, 2020.

(51) Int. Cl.
*C12N 7/00* (2006.01)
*C12M 1/12* (2006.01)
*C12M 1/34* (2006.01)

(52) U.S. Cl.
CPC ............... *C12N 7/00* (2013.01); *C12M 25/18* (2013.01); *C12M 41/12* (2013.01); *C12M 41/34* (2013.01); *C12M 41/36* (2013.01); *C12N 2760/20234* (2013.01); *C12N 2760/20243* (2013.01); *C12N 2760/20251* (2013.01)

(58) Field of Classification Search
CPC ............ C12N 7/00; C12N 2760/20251; C12N 2770/00051; C12M 41/12; C12M 41/00; C12M 41/34
See application file for complete search history.

(56) References Cited

FOREIGN PATENT DOCUMENTS

| WO | WO-03039459 A2 | 5/2003 |
|---|---|---|
| WO | WO-2013040445 A1 | 3/2013 |
| WO | WO-2019122239 A1 | 6/2019 |
| WO | WO-2020168230 A1 | 8/2020 |
| WO | WO-2022087509 A1 | 4/2022 |

OTHER PUBLICATIONS

Herzog et al. Plaque Assay for Human Coronavirus NL63 Using Human Colon Carcinoma Cells; Virology Journal, vol. 5, No. 138, pp. 1-9. (Year: 2008).*
Nie et al. Production Process Development of Pseudorabies Virus Vaccine By Using a Novel Scale-Down Model of a Fixed-Bed Bioreactor; Journal of Pharmaceutical Sciences, vol. 109, pp. 959-965. (Year: 2019).*
Cononel et al. Influenza A Virus Production in a Single-Use Orbital Shaken Bioreactor Aith ATF of TFF Perfusion Systems; Vaccine, No. 37, pp. 7011-7018. (Year: 2019).*
Han et al. High Density Vero Cell Perfusion Culture in Bioblu 5P Single-Use Vessels; Eppendorf, Application Note, No. 359, pp. 1-8. Downloaded from: https://www.eppendorf.com/product-media/doc/en/308208/Fermentors-Bioreactors_Application-Note_359_BioB on Jun. 28, 2023. (Year: 2017).*
Berrie et al., Development of a high-yield live-virus vaccine production platform using a novel fixed-bed bioreactor, Vaccine, vol. 38, No. 20, Apr. 1, 2020; pp. 3639-3645.
Clarke et al., Live Virus Vaccines Based on a Vesicular Stomatitis Virus (VSV) Backbone: Standardized Template with Key Considerations for a Risk/Benefit Assessment, Vaccine. Dec. 12, 2016; 34(51); pp. 6597-6609, Published online Jul. 6, 2016.
Hoeksema et al., Enhancing viral vaccine production using engineered knockout vero cell lines—A second look, Vaccine, vol. 36, No. 16, Mar. 16, 2018, pp. 2093-2103.
Humphreys et al., Novel viral vectors in infectious diseases, Immunology. Jan. 2018; 153 (1):1-9. Epub Sep. 26, 2017.
Jiang et al., Kinetic model for adherent Vero cell growth and poliovirus production in batch bioreactors, Process Biochemistry, vol. 81, Jun. 2, 2019, pp. 156-164.
PCT/US2021/056381 International Search Report and Written Opinion dated Feb. 18, 2022.

* cited by examiner

*Primary Examiner* — Jeanette M Lieb
*Assistant Examiner* — Paul C Martin
(74) *Attorney, Agent, or Firm* — Wilson Sonsini Goodrich & Rosati

(57) ABSTRACT

The invention relates to a method of increasing the yield of virus, virus particles, or viral vectors from host cells in a bioreactor. The invention provides a reproducible and robust method and system of determining and controlling the optimal time of infection of host cells using a correlation of process air parameters including Air flow, $O_2$ flow, and respective trends thereof resulting in increased virus yield.

24 Claims, 7 Drawing Sheets

METHOD FOR INFECTING CELLS WITH VIRUS

CROSS-REFERENCE TO RELATED APPLICATION

The application is a continuation of International Application No. PCT/US2021/056381, filed internationally on Oct. 23, 2021, which claims the benefit of U.S. Provisional Application No. 63/104,803, filed Oct. 23, 2020, all of which are hereby incorporated by reference herein in their entireties, including any figures, tables, nucleic acid sequences, amino acid sequences, or drawings.

FIELD OF THE INVENTION

The present invention relates to a method of propagating viruses and viral vectors for vaccine and viral vector manufacturing. More particularly, the invention relates to a specific method for initiation of host cell infection resulting in increased virus yield from host cells in a fixed-bed bioreactor.

BACKGROUND OF THE INVENTION

Robust technologies that allow reproducible and robust production of viruses and virus vectors to meet the ever-increasing demand for vaccines and other therapeutics are essential. In addition, for the development of versatile host cell technology platforms such as Vero cells and other mammalian cell platforms, avian cell platforms, and insect cell technology platforms, technologies that improve the virus yield from the host cells also play an important part in accelerating the development of the vaccine process and production. The present invention fulfills a need to improve methods of virus generation.

BRIEF SUMMARY OF THE INVENTION

Embodiments of the subject invention provide systems and methods for utilization of the air flow and $O_2$ flow parameters to determine the optimal time of infection for host cells expanding in fixed-bed and other bioreactor systems in which cell count sampling is difficult, impractical, or impossible.

Known methods for using metabolite data to determine the optimal time of infection in fixed-bed reactors with respect to the cell density require sampling and a broad infection window. Through observations of process air parameters, including comparing overall air flow to $O_2$ flow within a reactor, the inventors have identified factors, parameters, and trends of interest, including a trend where the volume of air flow into a fixed-bed reactor reduces and crosses an increasing trend of the $O_2$ flow volume into the reactor. The invention provides a reproducible and robust process of determining and controlling the optimal time of infection of host cells using a correlation of process air parameters including Air flow, O2 flow, and respective trends thereof resulting in increased virus yield. Data disclosed herein supports the Air/$O_2$ trend and correlation to cell density within the reactor.

DETAILED DESCRIPTION OF THE INVENTION

Figure 1:
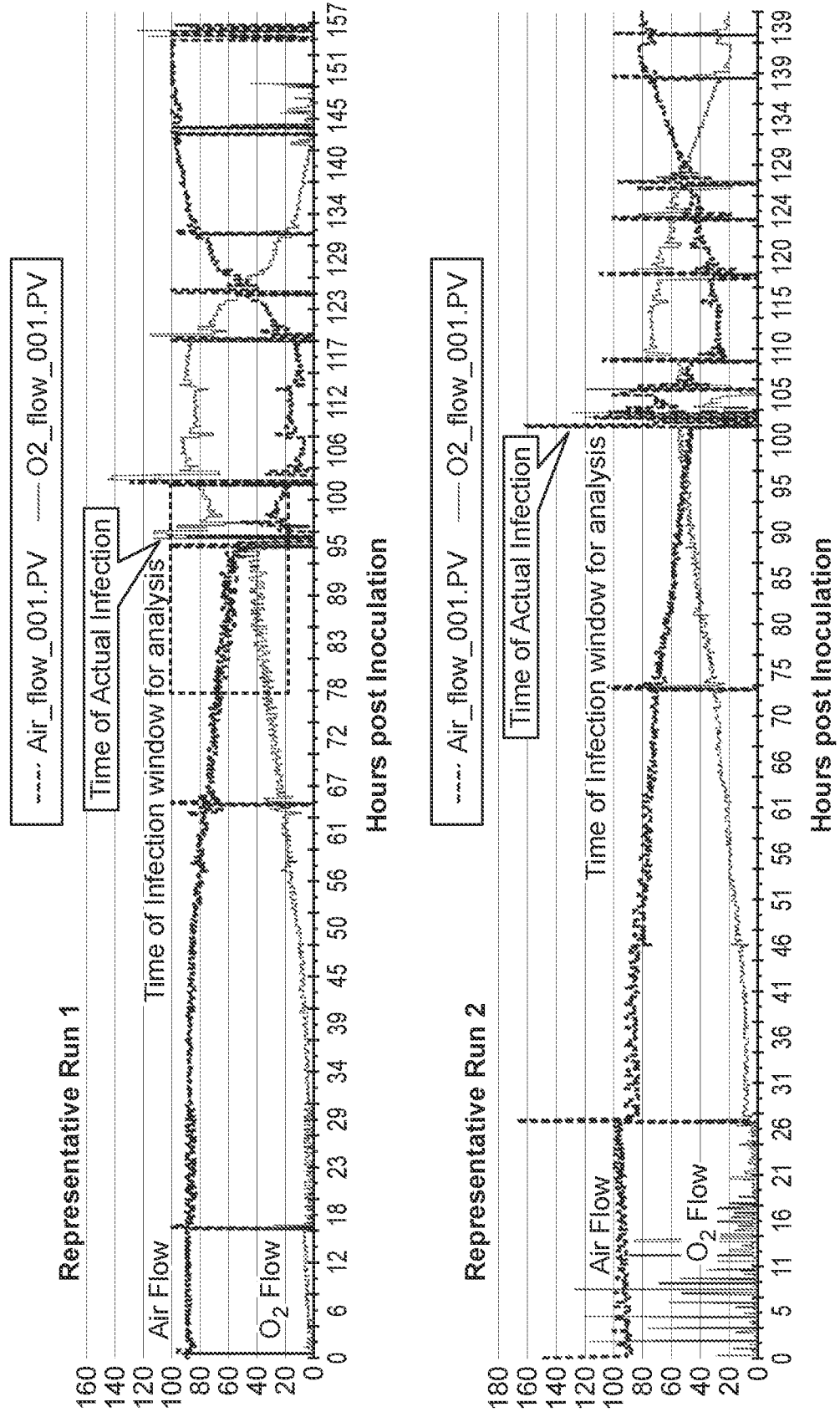
FIG. 1 compares air flow and oxygen ($O_2$) flow for two representative runs in accordance with embodiments of the subject invention.

The subject invention provides systems and methods for reproducible and robust process of determining and controlling the optimal time of infection of host cells using a correlation of process air parameters including Air flow, O2 flow, and respective trends thereof, resulting in increased virus yield.

In an embodiment, the subject invention provides a method of infecting host cells with a virus without a required step of counting the host cells, comprising the following steps: cultivating host cells in a bioreactor; observing a set of bioreactor process air parameters; identifying a first time-marker based on the bioreactor process air parameters; calculating, based on the first time-marker, an optimal time of infection window; and infecting the host cells during the calculated optimal time of infection window.

Equipment consistent with Current Good Manufacturing Practice (CGMP) may not be equipped for cell count. An advantage of the invention is that it provides a process that allows process monitoring to initiate optimal time of infection based on correlation of airflow and oxygen flow instead of, or in addition to, time, cell count, or surrogates of cell count (such as biomass).

In certain embodiments, the host cells may include adherent cells. In certain embodiments, the bioreactor may be a fixed-bed bioreactor. In certain embodiments the step of observing the bioreactor process air parameters comprises measuring a rate of total air flow into the bioreactor and measuring a rate of $O_2$ flow into the bioreactor at a plurality of time points, to create a current measurement set at each respective time point. In certain embodiments the step of identifying a first time-marker comprises determining a time at which the rate of total air flow into the bioreactor reduces and crosses an increasing trend of the rate of $O_2$ flow into the bioreactor. In certain embodiments the step of identifying a first time-marker comprises calculating one or more values from one or more current measurement sets to predict a future time at which the rate of total air flow into the bioreactor is expected to reduce and cross an expected increasing trend of the rate of $O_2$ flow into the bioreactor.

Optionally, once an infection window is established for a specific cell line and virus, the established infection window can be applied and utilized with other viruses. However, it may still be desirable to monitor rates of total air flow into the bioreactor and $O_2$ flow into the bioreactor for active monitoring to gather data and for process control in real-time.

The type of host cell used for the cultivation of virus in the invention may be natural or genetically modified (e.g., recombinant cell, cell line, etc.), and may be any eukaryotic cell that is suitable for the production of virus antigen, viral vector, or virus production. In some embodiments, the host cells are Vero cells, and the virus is a viral vector such as recombinant vesicular stomatitis virus (rVSV).

In some embodiments, determination of the optimal time of infection window is based on a correlation of process air parameters including but not limited to Air flow, $O_2$ flow, and convergence thereof, relationships there between (e.g., ratios there between), or respective trends thereof, resulting in increased virus yield. In some embodiments, the optimal time of infection window is the convergence of air flow and $O_2$ flow. In some embodiments, the infection window is the time interval in which airflow decreases and $O_2$ flow increases such that they are within ±30% of each other, or within ±20% of each other, or within ±10% of each other, or within ±5% of each other.

Embodiments of the invention include a method of producing virus in a bioreactor comprising the following steps: providing host cells in the bioreactor; growing the host cells in the bioreactor; observing a set of bioreactor process air parameters; calculating, based on the set of bioreactor process air parameters, an optimal time of infection window; infecting the host cells with at least one virus or virus particle during the optimal time of infection window; incubating the host cells infected with the virus or virus particle to propagate the virus; and, optionally, harvesting the virus.

In some embodiments, the host cells are adherent cells. In some embodiments, the bioreactor is a flat-bed bioreactor, and the step of growing the host cells is carried out at a constant initial dissolved oxygen ($dO_2$) level, pH, and temperature. In certain embodiments the bioreactor is a single-use flat-bed bioreactor.

In certain embodiments, alone or in combination with any preceding embodiment, calculating the optimal time of infection window comprises determining a time at which the rate of total air flow into the bioreactor reduces and crosses or intersects with an increasing trend of the rate of $O_2$ flow into the bioreactor. In alternate embodiments alone or in combination with any preceding embodiment, calculating the optimal time of infection window comprises determining a time at which an Air-$O_2$ Difference of the bioreactor is approaching zero or is zero. In other embodiments alone or in combination with any preceding embodiment, calculating the optimal time of infection window comprises determining a time at which an Air-$O_2$ Difference of the bioreactor is less than a predetermined threshold or is expected to cross below the predetermined threshold. In some embodiments, the optimal time of infection window is the convergence of air flow and $O_2$ flow. In some embodiments, the infection window is the time interval in which airflow decreases and $O_2$ flow increases such that they are within ±30% of each other, or within ±20% of each other, or within ±10% of each other, or within ±5% of each other.

Considering convergence, and referring to Representative Run 1 in FIG. 1 as a non-limiting example: A convergence threshold of +/−30 units (e.g., mL/min) may be selected for this run. When airflow is 80 (e.g., mL/min) and $O_2$ flow is 20 (e.g., mL/min), then 80−20=60 convergence is not achieved and the window of infection is not met. When airflow is 66 and $O_2$ flow is 38, then 65−38=27, convergence is achieved and the window of infection is met (in this example, this is the first point of the dashed box around time of infection window). When airflow is 60 and $O_2$ flow is 40, then 60−40=20, convergence is achieved and the window of infection is met (in this example, this is the later point of the dashed box around time of infection window). For this run, this is when infection occurred. Note that in certain embodiments, additional parameters may be applied, such as requiring a minimum time of convergence, a tighter window (lower threshold) of convergence, or convergence together with another value before infection.

Referring now to Representative Run 2 in FIG. 1, as a non-limiting example: A convergence threshold of +/−30 units (e.g., mL/min) may be selected for this run. When airflow is 80 and $O_2$ flow is 20, then 80−20=60, convergence is not achieved and the window of infection is not met. When airflow is 60 and $O_2$ flow is 30, then 60−30=30, convergence is achieved and the window of infection is met (this is the first point of the dashed box around time of infection window. When airflow is 50 and $O_2$ flow is 50, then 50−50=0, convergence (in this case also the intersection point) is achieved and the window of infection is met (this is the intersection point of the dashed box around time of infection window. When airflow is 40 and $O_2$ flow is 60, then 40−60=−20, convergence is achieved and the window of infection is met (this is the later point of the dashed box around time of infection window). For this run, this is when infection occurred. Note that in certain embodiments additional parameters may be applied, such as requiring a minimum time of convergence, a tighter window (lower threshold) of convergence, or convergence together with another value (such as a specific absolute value of either airflow or $O_2$ flow) infection.

Advantageously, this method of infecting host cells based on air flow and $O_2$ flow rates makes virus production controlled and reproducible based on process monitoring and allows use of a closed system without the need for cell counting. As a closed system, the bioreactor is a self-sufficient environment that is enclosed during operation (e.g., hermetically sealed), allowing continuous culture, without the need for cell counting or the need for access ports for cell counting.

Alternatively, infection of the host cells may be based on time derived from historical data using the invention, but without active monitoring.

In some embodiments, the host cells provided (e.g., seeded) into the bioreactor are not counted prior to the infecting step. In some embodiments, the methods further comprise harvesting the host cells or a product of the host cells after infection. In some embodiments, the host cells in the bioreactor are not counted prior to harvesting.

In some embodiments, the bioreactor does not include a cell counting device (e.g., instruments such as a counting chamber, automated cell counter, Coulter counter, or cytometer such as a flow cytometer), and is not connected to a cell counting device. Cell counting devices may utilize a range of techniques, such as image-based counting (e.g., bright field or fluorescence) or non-image-based counting (e.g., electrical current exclusion). In some embodiments, the bioreactor does not have an access port for cell counting. In some embodiments, the bioreactor is a closed, sealed (e.g., hermetically sealed) system.

In certain embodiments the infection of the host cells with the virus is at multiplicity of infection (MOI) of about 0.1 to 0.05. In certain embodiments the infection of the host cells with the virus is at MOI of 0.05. In certain embodiments the step of incubating the host cells infected with the virus or virus particle to propagate the virus comprises incubating the host cells in a constant final $dO_2$ level, pH, and temperature which is different from the constant initial $dO_2$ level, pH, and temperature.

The virus may be any naturally occurring or genetically modified virus (e.g., recombinant or engineered virus). In certain embodiments, the virus is selected from a group consisting of naturally occurring or genetically modified VSV, adenovirus, Influenza virus, Ross River virus, Hepatitis A virus, Vaccinia virus, Herpes Simplex virus, Japanese Encephalitis virus, Herpes Simplex virus, West Nile virus, Yellow Fever virus, Rhino virus, Reovirus, Ebola-Zaire virus, Ebola-Sudan virus, Ebola-Marburg virus, Nipah virus, or chimeras of any of the foregoing. In some embodiments, the virus is a viral vector. In certain embodiments, the virus is a VSV vector. In certain embodiments, the virus is a modified viral vector, such as VSV, containing glycoprotein from another virus of interest.

The type of host cell used for the cultivation of virus in the invention may be natural or genetically modified (e.g., recombinant cell, cell line, etc.), and may be any eukaryotic cell that is suitable for the production of virus antigen, viral vector, or virus production. In some embodiments, the host cells are selected from among naturally occurring or genetically modified mammalian cells (e.g., human cells and murine cells), avian cells (e.g., chicken cells and quail cells), and insect cells.

In some embodiments the host cells are selected from the group consisting of Vero cells, MBCK cells, MDBK cells, MRC-5 cells, BSC-1 cells, LLC-MK cells, CV-1 cells, CHO cells, COS cells, HeLa cells, HEK 293 cells, MDOK cells, CRFK cells, RAF cells, TCMK cells, LLC-PK cells, PK 15 cells, Wl-38 cells, T-FLY cells, BHK cells, SP2/0 cells, NS0 cells, PerC6 cells, COR cells, and QOR cells.

In certain embodiments, the host cells are Vero cells or HEK 293 cells.

Optionally, the method of the invention includes steps beyond host cell expansion, infection, and optional harvest. For example, in some embodiments, the method may further include the step of determining a virus titer by plaque assay method; the step of purifying and or characterizing the virus; or the step of producing a vaccine, viral vector for gene delivery, or immunotherapeutic composition with the cells, or cell-derived products such as virus, or a portion of the virus. The invention includes compositions such as vaccines and immunotherapeutic compositions produced by the method, which may be formulated for administration to a human or animal subject by any suitable route of administration.

For example, to produce a composition such as a vaccine, vector, or immunotherapeutic composition, the harvested cells or cell-derived products (such as virus or a portion thereof, or other biomolecules) may be combined with one or more excipients, diluents (such as water, phosphate buffered saline, or saline), carriers, adjuvants, or any combination of two or more of the foregoing. The adjuvant may be of any class suitable for the vaccine or composition's intended use, such as alum salts and other mineral adjuvants, bacterial products or bacteria-derived adjuvants, tensoactive agents (e.g., saponins), oil-in-water (o/w) and water-in-oil (w/o) emulsions, liposome adjuvants, cytokines (e.g., IL-2, GM-CSF, IL-12, and IFN-gamma), and alpha-galactosylceramide analogs. Some non-limiting examples of adjuvants include Montanide emulsions, QS21, Freund's complete or incomplete adjuvant, aluminum phosphate, aluminum hydroxide, Bacillus Calmette-Guerin (BCG), and alum.

Optionally, the method may further include harvesting cells, and harvesting cell-derived products from the infected host cells, using methods known in the art. Various biomolecules produced by naturally occurring or non-genetically modified cells that are produced using the methods of the invention can be harvested (e.g., isolated from the biomolecule-producing cells) for various uses, such as the production of drugs or biologics, and for pharmacological studies. Thus, using the invention, cells can be used as biological "factories" to provide the products of the cells, such as biomolecules. The term "biomolecule" refers to a molecule or molecules that can be produced by cells (a cell-derived product). Such biomolecules include, but are not limited to, proteins, peptides, amino acids, lipids, carbohydrates, nucleic acids, nucleotides, viruses, portions of virus (e.g., viral particles), and other substances. The biomolecules can be intracellular, transmembrane, or secreted by the cells, for example, and may be purified or isolated using methods known in the art.

The capacity of the bioreactor can be any that meets the production purpose, e.g., for screening, laboratory research and development, clinical studies, and commercial production. A variety of types, sizes, and models of suitable bioreactors are commercially available. Examples of commercially available bioreactors that may be used in the invention include, but are not limited to, the single-use, fixed-bed bioreactors produced by Univercells Technologies and iCELLis.

In some embodiments, the bioreactor has a capacity in the range of 1 $m^2$-600 $m^2$ (as surface area), alternatively 10 $m^2$-30 $m^2$, alternatively 30 $m^2$-200 $m^2$, alternatively 200 $m^2$-600 $m^2$, alternatively 600 $m^2$-2400 $m^2$, alternatively 2.4 $m^2$-2400 $m^2$. In some embodiments, the bioreactor has a volume capacity of 700-800 mL (e.g., iCELLis nano). In some embodiments, the bioreactor has a volume capacity of 25 L-50 L (e.g., iCELLis 500). In some embodiments, the bioreactor has a capacity of 10 $m^2$-30 $m^2$ or volume capacity of 1.5 L-3.5 L (e.g., UNVC carbo). In some embodiments, the bioreactor has a capacity of 200 $m^2$-600 $m^2$ or volume capacity of 30 L-100 L (e.g., UNVC nitro). In some embodiments, the bioreactor has a capacity of about 2,400 $m^2$ or volume capacity of 350 L-400 L (e.g., UNVC oxo), or more.

The media can be any media suitable for the host cells and the production purpose, such as serum-free chemically defined media.

Embodiments of the method of the invention may include the following steps: providing host cells in the bioreactor; growing host cells in a constant initial $dO_2$ level, pH, and temperature to confluence; calculating, based on the set of bioreactor process air parameters, an optimal time of infection window; infecting the host cells with at least one virus or virus particle during the optimal time of infection window; incubating the host cells infected with the virus or virus particle to propagate the virus; and, optionally, harvesting the virus.

Embodiments may advantageously employ a correlation between factors including air flow and the flow of $O_2$, with the cell density in the bioreactor. This correlating trend may be used to better determine the optimal time of infection in fixed-bed reactors (e.g., including reactors that do not allow for cell count sampling, or for which cell counting is impractical).

Turning now to the figures, FIG. 1 compares air flow and oxygen ($O_2$) flow for two representative runs of a fixed bed bioreactor system in accordance with embodiments of the subject invention.

Figure 2:
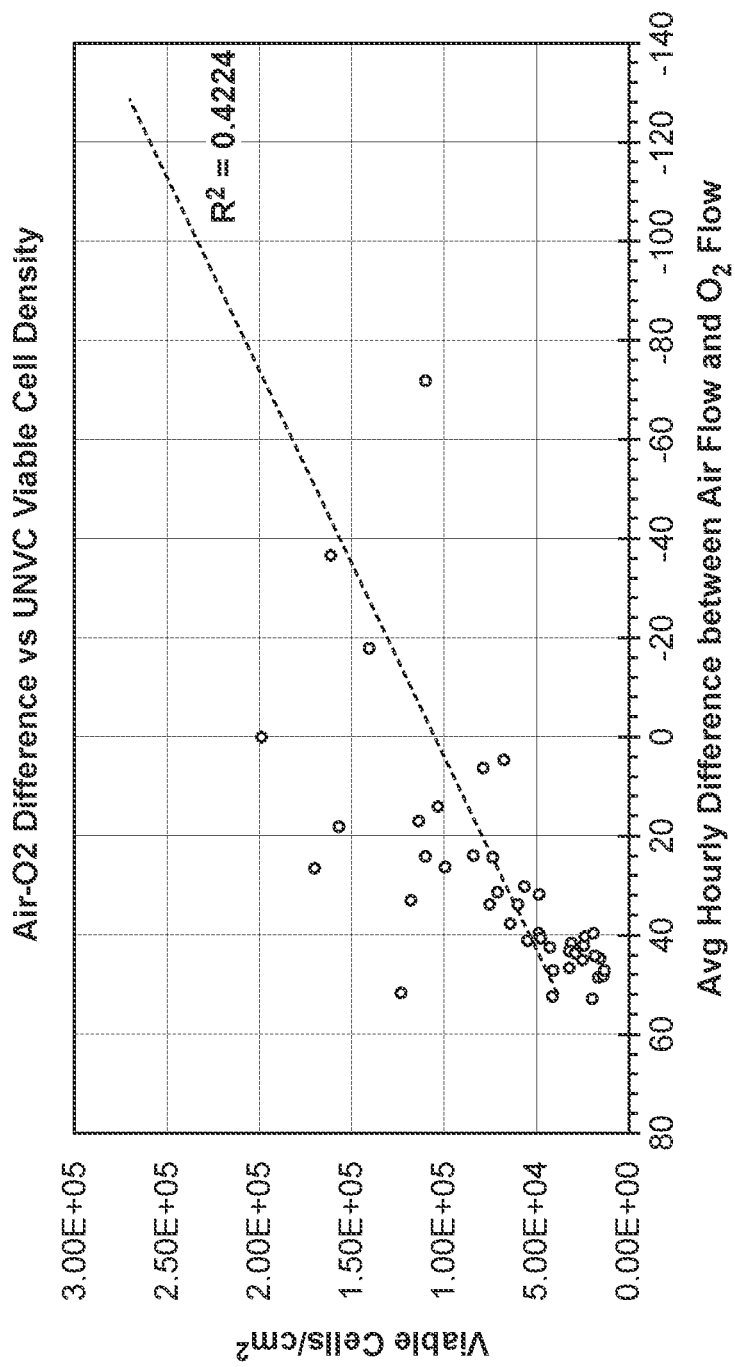
FIG. 2 charts Air-$O_2$ Difference versus UNVC Viable Cell Density in accordance with embodiments of the subject invention.

FIG. 2 charts Air-$O_2$ Difference versus Univercells (UNVC) Viable Cell Density in accordance with embodiments of the subject invention. Embodiments may evaluate the difference between Air Flow rate and $O_2$ Flow rate. In this instance, a positive difference indicates air flow volume is greater than $O_2$ flow volume, while a negative difference would indicate the opposite, or air flow volume is less than $O_2$ flow volume. When air flow volume is equal to $O_2$ flow volume, the difference is zero.

In this chart, as the difference (d) approaches zero, viable cell density (VCD, measured here in viable cells per square centimeter) approaches $1\times10^5$ cells/cm$^2$. Around d=20, VCD is within half a log of $1\times10^5$ cells/cm$^2$ which is known as the "infection trigger point." Embodiments may use the trends of Air Flow and $O_2$ Flow to estimate the time required for infection. In this example, using d retains approximately 42% of the variability of VCD, $R^2$=0.4224, and the Difference: VCD Correlation Coefficient=−0.64.

Figure 3:
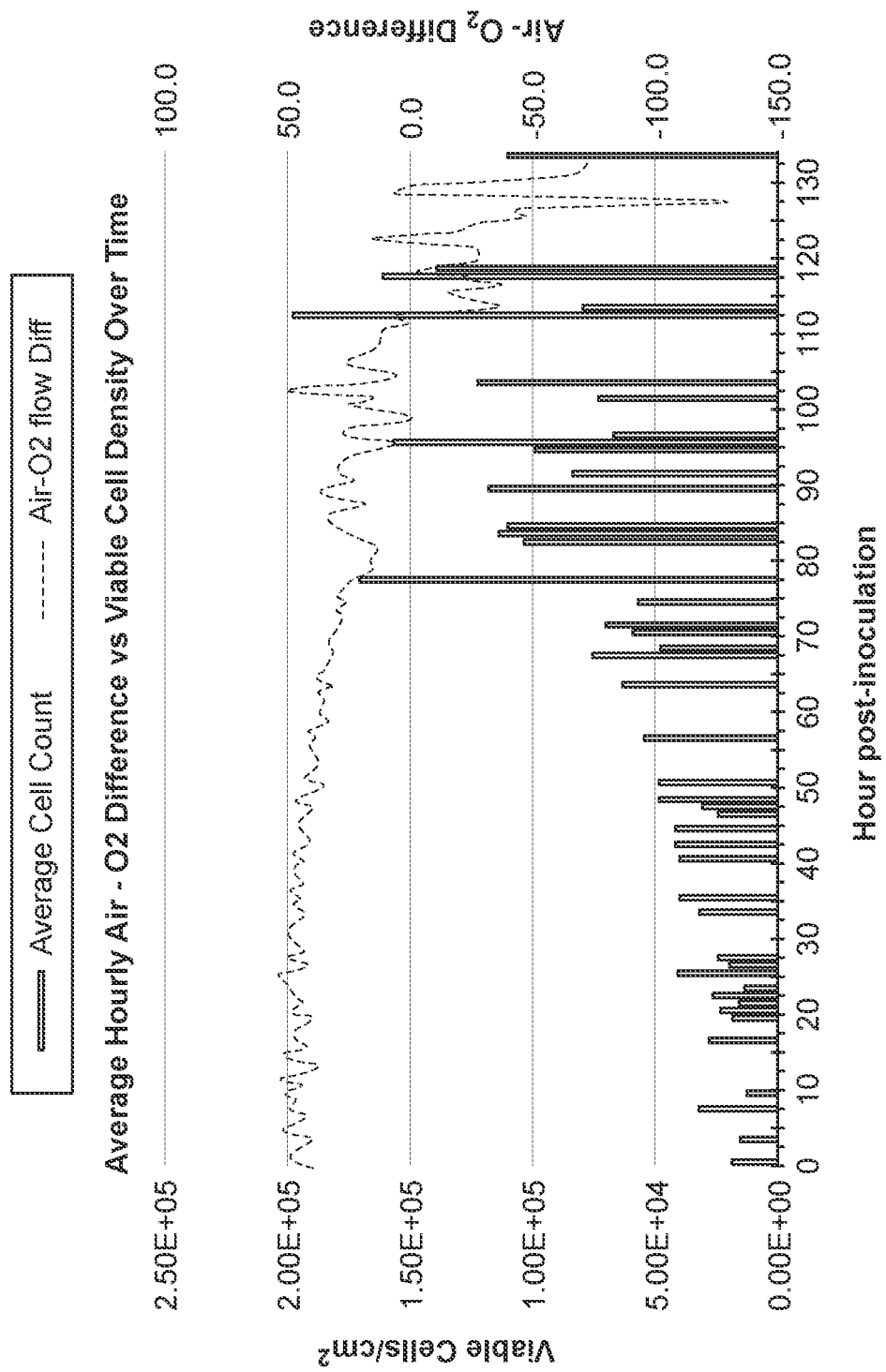
FIG. 3 charts Average Hourly Air-$O_2$ Difference vs Viable Cell Density Over Time in accordance with embodiments of the subject invention.

FIG. 3 charts Average Hourly Air-$O_2$ Difference versus Viable Cell Density Over Time in accordance with embodiments of the subject invention, comparing the air-$O_2$ difference on the right-hand axis vs VCD (cells/cm$^2$) on the left-hand axis with respect to time (hours post-inoculation, or hpi) on the x-axis. By 64 hpi, historical VCD has shown to between $5\times10^4$ and $1\times10^5$ cells/cm$^2$. Within a window of 84-96 hpi, VCD tends to be closest to $1\times10^5$ cells/cm$^2$. At this window, Air and $O_2$ trending lines begin to converge. Embodiments of the subject invention may advantageously provide a more reliable estimate of optimal time for infection.

Figure 4:
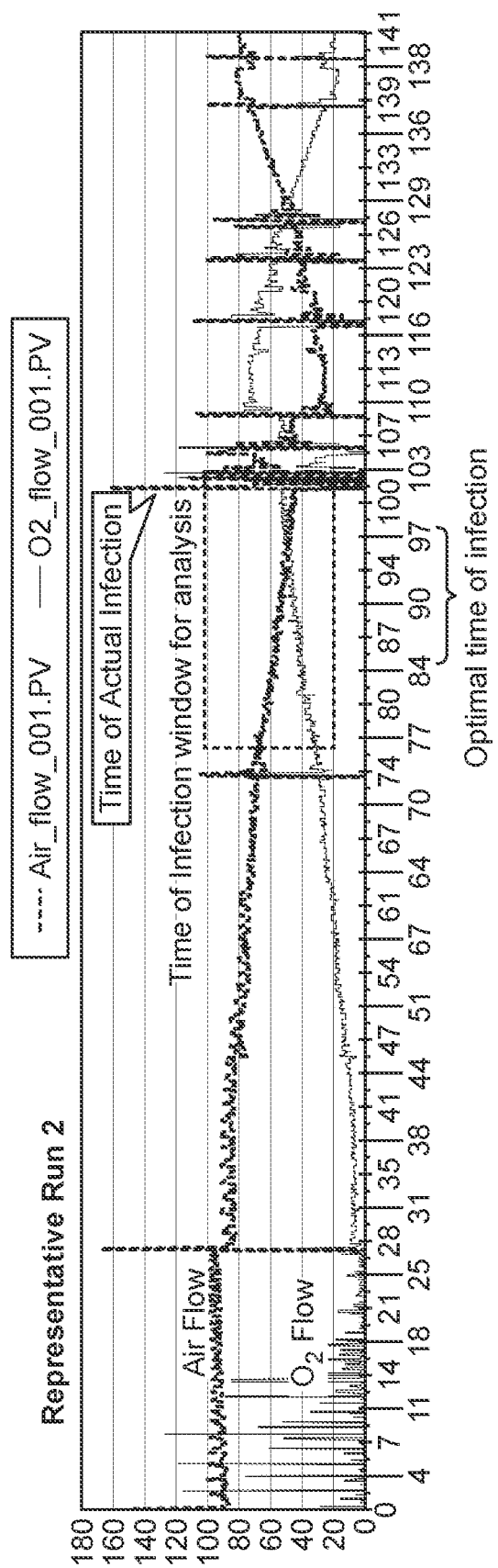
FIG. 4 illustrates an Air-$O_2$ Difference model applied to Representative Run 2 from FIG. 1 according to embodiments of the subject invention.

FIG. 4 illustrates an Air-$O_2$ Difference model applied after the fact to data collected from Representative Run 2 (as shown in FIG. 1) according to embodiments of the subject invention. Extrapolating the analyses to representative Run #2 suggests that the actual time of infection occurred later than the optimal time of infection. In this example, the infection occurred when the cells were at a density of $1.3\times10^5$ viable cells/cm$^2$, which is a higher cell density than the target density of $1\times10^5$ cells/cm$^2$.

Figure 5A:
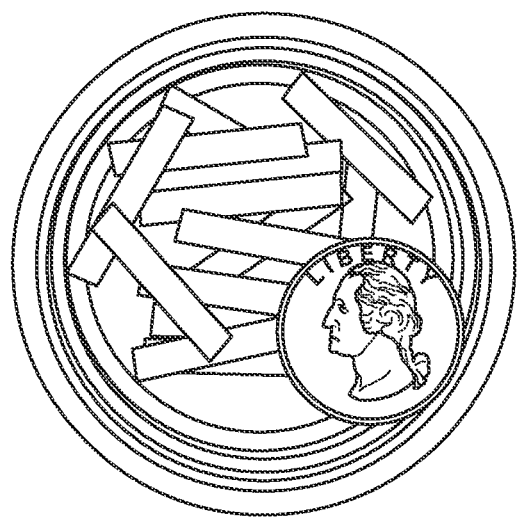
FIG. 5A illustrates microcarrier strips that are used in a fixed-bed bioreactor, 13 microcarrier strips of about 11.2 $cm^2$ 3-dimensional area per strip are shown in 5 mL of media.

FIG. 5A illustrates microcarrier strips that are used in a fixed-bed bioreactor, 13 microcarrier strips of about 11.2 cm$^2$ 3-dimensional area per strip are shown in 5 mL of media.

Figure 5B:
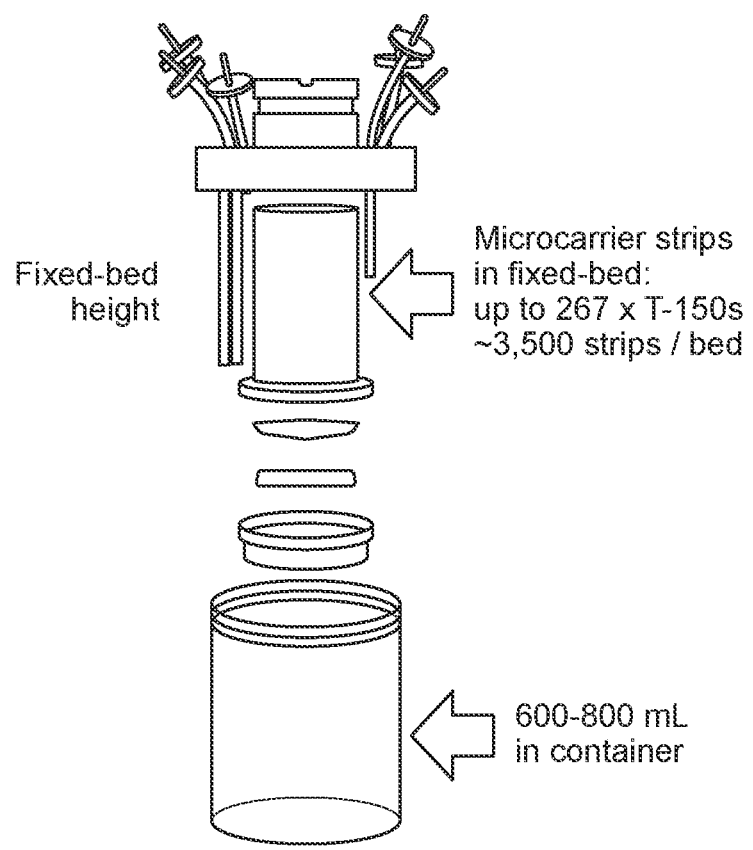
FIG. 5B illustrates a cross-section of a bioreactor that may be used to hold up to 3,500 strips per bed.

FIG. 5B illustrates a cross-section of a bioreactor that may be used to hold up to 3,500 strips per bed.

Figure 5C:
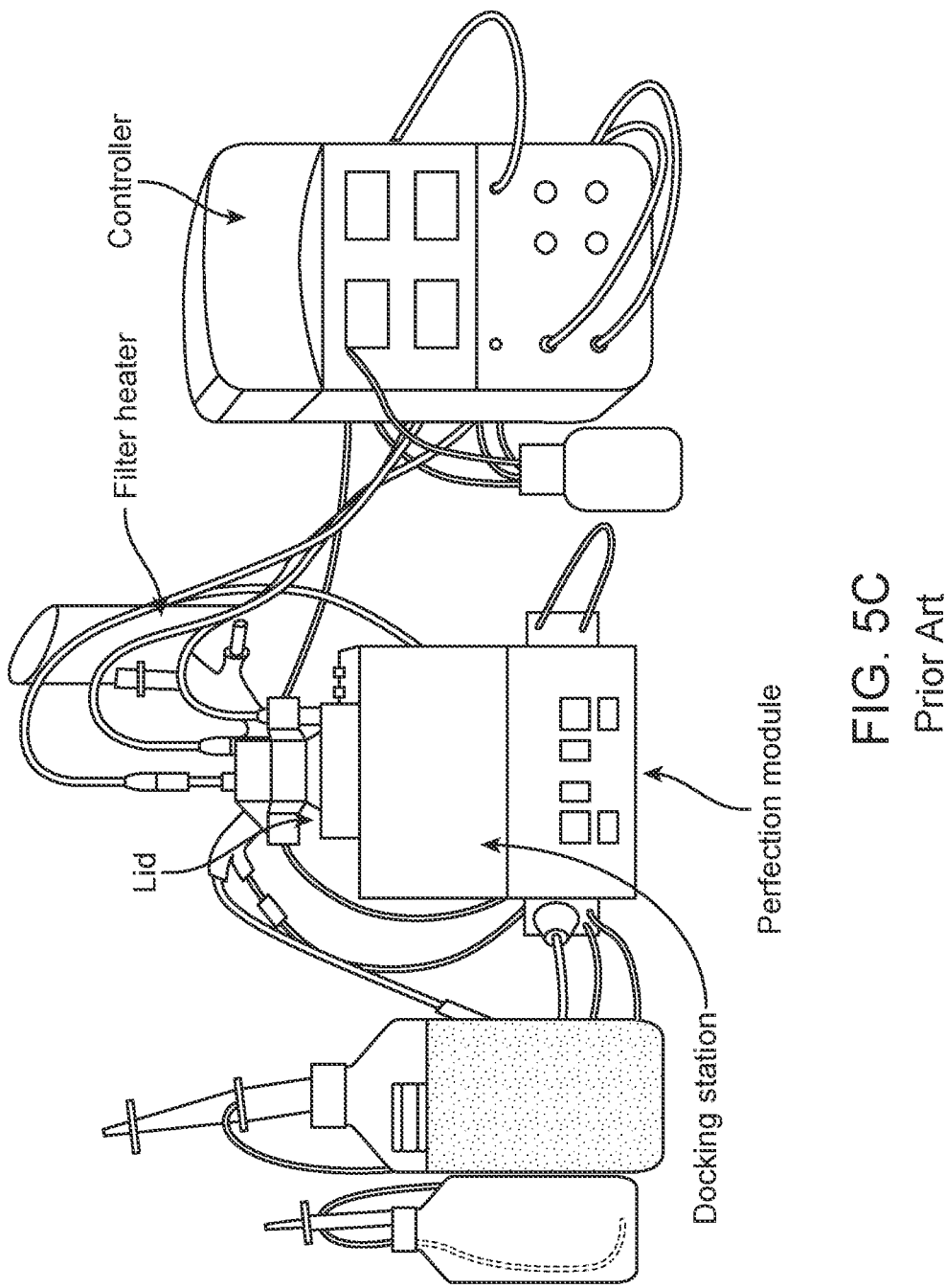
FIG. 5C illustrates the different parts of a bioreactor in a cross-sectional view.

FIG. 5C illustrates the different parts of the bioreactor in a cross-sectional view.

The invention provides a method of infecting host cells with a virus without a required step of counting the host cells. In particular, the invention provides a reproducible and robust process of determining and controlling the optimal time of infection of host cells resulting in increased virus yield. In one embodiment, the method comprises of the steps: 1) providing (e.g., seeding) host cells in a bioreactor in an environment where system parameters such as total air flow, $O_2$ flow, dissolved oxygen (dO$_2$), pH, and temperature can be measured and controlled, 2) growing the host cells at a first set of pre-infection system parameters, 3) monitoring the system parameters, 4) infecting the host cells with at least one virus at a time determined at least in part by a change in two or more of the measured system parameters, incubating the host cell with the virus at a second set of post-infection system parameters, and, optionally, 5) harvesting the virus. In some embodiments, the host cells are adherent cells that are anchorage-dependent and require a flat surface, microcarriers, and/or a fixed-bed to anchor. In particular embodiments, Vero cells or HEK 293 cells are used as host cells in a fixed-bed bioreactor.

In some embodiments, the method includes the steps of: 1) providing (e.g., seeding) host cells into bioreactor at a constant initial 80-100% dO$_2$, 7.2-7.4 pH and 36° C.±2° C. temperature, 2) decreasing the dO$_2$ level up to 50% of the initial dO$_2$ level, while keeping the pH and temperature constant, 3) infecting the host cells with at least one virus during an infection window defined as when airflow decreases and oxygen flow increases such that they are within ±20% of each other, 4) incubating the host cell with the virus at dO$_2$ level of 20-50%, 7.2-7.4 pH and 36° C.±2° C. temperature, and optionally 5) harvesting of virus.

In a specific embodiment of the invention, the dO$_2$ is decreased at least 50% at 12 hours before infecting the host cells with a virus. In an embodiment, the host cells are infected with the virus after the host cells are grown to the highest cell density. In yet another embodiment of the invention, the dO$_2$ is decreased after the host cells have reached the highest cell density.

The quantity of virus produced by this method is more reproducible and significantly more than that produced in a conventional method where all the parameters including dO$_2$ are kept constant throughout the process.

The following applies to the detailed description section of this application.

Where an indefinite or definite article is used when referring to a singular noun, e.g., "a", "an" or "the", this includes a plural of that noun unless something else is specifically stated.

In the context of the present invention, the terms "about" or "approximate" denote an interval of accuracy that the person skilled in the art will understand to still ensure the technical effect of the feature in question. When used in conjunction with a numerical value, the term typically indicates a deviation from the indicated numerical value of ±10%, and preferably of ±5%.

As used herein, the term "bioreactor" refers to a device that supports a biologically active environment in which a biological process such as propagation of virus and vectors under controlled conditions may be carried out. Bioreactors may be designed for small-scale cultures such as those used in research laboratories, as well as large-scale bioreactors comprising vessels or vats to produce and harvest biological macromolecules such as vaccine virus, antigens, and vectors on a pilot plant or commercial scale. A bioreactor may be used to propagate both suspended and adherent cells. The bioreactor is a controlled environment wherein the oxygen/dO$_2$, nitrogen, carbon dioxide, and pH levels may be adjusted.

A "fixed-bed bioreactor" means a type of bioreactor which includes a fixed-bed of packing material that promotes cell adhesion and growth. Fixed-bed bioreactors have been used to produce viral vaccine products at both small and large-scale due to the ability to perfuse high-cell densities with low shear force. Any configuration or platform of fixed-bed bioreactor may be used with the invention.

The fixed-bed bioreactor may be a single-use bioreactor such as the commercially available iCELLis system (Pall Corporation) or scale-X™ system (Univercells), which are described in Berrie D M et al., *Vaccine*, 2020, 38:3639-3645, which is incorporated herein by reference in its entirety. The iCELLis system platform offers a novel fixed-bed technology comprising carriers composed of woven medical-grade polyethylene terephthalate (PET) fibers in a robust, single, closed system that does not require any aseptic handling. Additionally, this system incorporates high rates of gas exchange using "waterfall" technology through the control of temperature, $O_2$, pH, carbon dioxide (CO$_2$), and nitrogen (N$_2$), in addition, the use of a magnetic impeller that produces low cell shear stress and evenly distributed media circulation. For most viruses, production titers from the iCELLis system are significantly increased when compared to classical adherent cell flat-stock flasks. The iCELLis technology may be used at small-scale such as in the iCELLis Nano, where the growing area is between 0.5 to 4 m² and manufacturing scale, such as in iCELLis 500 where the growing area ranges from 66 to 500 m². Processes developed in the small-scale system may be scaled up to that of the manufacturing scale.

The scale-X™ bioreactor system of Univercells oilers a range of growth surfaces: scale-X "hydro" (<3 m²) "carbo" (10-30 m²) and "nitro" (200-600 m²). This range offers a scalable process and the capability for clinical lot production. Within the Univercells product line, the bioreactor height increases, while the diameter is held constant. For the fixed-bed bioreactor is a commercially available iCELLIS Nano (Pall Corporation), iCELLis 500 bioreactor (Pall Corporation), or a Univercells fixed-bed bioreactor (Univercells SA). In some embodiments, the fixed-bed may provide a maximum of 40,000 cm² in an 800 mL fixed-bed bioreactor such as the iCELLis Nano, and up to 5,000,000 cm² in a 25 L fixed-bed bioreactor such as iCELLis 500 (FIG. 5A-C; Table 1). The fixed-bed height may range from 20 mm and 10 mm, providing a growth area of 5300 cm² to 40,000 cm² in an 800 mL fixed-bed bioreactor to 660000 cm² to 5,000,000 cm² in a 25 L fixed-bed bioreactor.

TABLE 1

| Compaction (strips per bed) | iCELLis Nano: 800 mL | | | | iCELLis 500: 80 L | | | |
|---|---|---|---|---|---|---|---|---|
| Total Surface | Low | | High | | Low | | High | |
| Area/Equivalent T-150 | cm² | T-150s | cm² | T-150s | cm² | T-150s | cm² | T-150s |
| Fixed-bed height—20 mm | 5,300 | 35 | 8,000 | 53 | 6.60E+05 | 4,400 | 1.00E+06 | 6,666 |
| Fixed-bed height—40 mm | 10,600 | 70 | 16,000 | 1065 | 1.33E+06 | 8,867 | 2.00E+06 | 13,333 |
| Fixed-bed height—100 mm | 26,000 | 173 | 40,000 | 267 | 3.03E+06 | 22,000 | 5.00E+06 | 33,333 | example, the carbo 10 m² bioreactor is ⅓ the height of a 30 m² bioreactor. However, scale-up among the different lines is achieved by keeping the height of the fixed-bed constant and increasing the diameter, similar to scale-up in chromatography systems. For instance, a 200 m² bioreactor is the same height as a 10 m² bioreactor, but the diameter is different. The scale-X carbo system is a single-use bioreactor coupled with in-line product concentration operated by a bench-scale automated process controller (pH, DO, T, agitation, liquid flow rates), which enables the production and simultaneous concentration of viral products; a feature that is novel and differentiates this type of fixed-bed bioreactor from others in the market. The fixed-bed in the scale-X carbo bioreactor offers surface areas for cell growth between 10 m² and 30 m² in a total vessel volume of 1.6-3.2 L, dependent on the surface area. This results in the capacity for a high cell density per unit volume and a compact footprint allowing integration in a standard biosafety cabinet. Many commercially available fixed-bed bioreactors use randomly packed disks or fabric strips as the substrate for cell attachment; however, the scale-X bioreactor utilizes a fixed-bed that is organized with a mesh layer which provides uniformity and vessel-to-vessel consistency for cell growth. A fixed-bed bioreactor may have sensors that measure and monitor the pH, temperature, dissolved oxygen, and the biomass, which indicates adherent cell density. A fixed-bed bioreactor may also have different ports that enable the addition of oxygen or nitrogen, a media exchange port, ports for the addition of sodium hydroxide (NaOH) and/or $CO^2$ to adjust the pH. The $dO_2$ of the media may be modified by addition of $O^2$ or $N^2$. Preferably the $dO_2$ levels may be depleted in a controlled manner by injecting $N_2$ in the headspace of the bioreactor, simultaneously stirring and monitoring the $dO_2$.

The host cell used in the invention may be an anchorage-dependent cell or adapted to be an anchorage-dependent cell line. The host cells of the disclosed method may be cultivated on microcarriers, which may be in suspension in bioreactors or on microcarrier strips. In some embodiments, the host cells are cultivated on microcarrier strips in a fixed-bed of a fixed-bed bioreactor. In some embodiments, Host cells may be cultivated by using a seeding density ranging from 2,000 to 20,000 cells per cm². The seeding density may be adjusted based on the type of host cell, the volume of the bioreactor, the height of fixed-bed in a fixed-bed bioreactor, etc. It is within the knowledge of one skilled in the art to select the optimum seeding density for the process. The growth of metabolically active cells may be monitored by correlation of process air parameters including but not limited to Air flow, $O_2$ flow, and convergence thereof, relationships there between (e.g., ratios there between), or respective trends thereof, resulting in increased virus yield.

The invention may include measuring further parameters such as biomass using a biomass sensor within the fixed-bed of the bioreactor. The biomass, which indicates the mass of the adherent cells, through conductivity, may be utilized to monitor the overall growth of host cells and the decrease in the cell mass due to the propagation of virus after infection. Higher biomass indicated by higher conductivity as monitored by the biomass sensor, indicates a higher growth rate of the cells. Reliance on biomass measurements has shortcomings, however. Biomass is not representative of metabolic activity or peak production. For example, host cells may fall into senescence and still register a high biomass. In addition, biomass measurement in some systems require accessing the bioreactor, which may present challenges for clinical and commercial processes, including CGMP compliance.

As used herein, "culture media" or "media" refers to a liquid used to culture the host cells in the bioreactor. The media used in the procedure of the disclosure may include various ingredients that support the growth of the host cells, including but not limited to amino acids, vitamins, organic and inorganic salts, carbohydrates. The media may be serum-free media, which is media formulated without any animal serum. A serum-free media when used may be selected from among DMEM, DMEM/F12, Medium 199, MEM, RPMI, OptiPRO SFM, VP-SFM, VP-SFM AGT, HyQ PF-Vero, MP-Vero, or others. The culture media may also be animal-free media; that is, it does not have any product of animal origin. The culture media may also be protein-free media; that is, the media is formulated with no proteins. The serum-free or protein-free media may be formulated without serum or protein but may contain cellular protein derived from the host cells, and optionally proteins specifically added to the serum-free or the protein-free media.

The pH for cultivation can be, for example, between 6.5-7.5, depending on the pH stability of the host cells. Preferably the cells are cultivated at a pH of 7.4. The host cells may be cultivated at the temperature between 20-40° C., specifically between 30° C. and 40° C., and preferably at 36° C.±1° C. for mammalian cells.

The host cell or host cell line or cells used for the cultivation of virus in the method of the disclosure may be any eukaryotic cell that is suitable for the production of virus antigen, viral vector, or virus production. Preferably the host cell may be "adherent cell" or an "anchorage-dependent cell." Adherent cells are cells that adhere to a surface in culture condition, anchorage may be required for their grown, and they may also be called anchorage-dependent cells.

The host cells used in the invention may be natural or genetically modified (e.g., recombinant cell, cell line, etc.), and may be any eukaryotic cell that is suitable for the production of virus antigen, viral vector, or virus production. In some embodiments, the host cells are selected from among naturally occurring or genetically modified mammalian cells (e.g., human cells and murine cells), avian cells (e.g., chicken cells and quail cells), and insect cells.

In some embodiments the host cells are selected from among Vero cells, MBCK cells, MDBK cells, MRC-5 cells, BSC-1 cells, LLC-MK cells, CV-1 cells, CHO cells, COS cells, HeLa cells, HEK 293 cells, MDOK cells, CRFK cells, RAF cells, TCMK cells, LLC-PK cells, PK 15 cells, Wl-38 cells, T-FLY cells, BHK cells, SP2/0 cells, NS0 cells, PerC6 cells, COR cells, and QOR cells.

In certain embodiments, the host cells are Vero cells or HEK 293 cells.

The preferred adherent cell is an anchorage-dependent cell that may be grown on a carrier such as a PET strip, but suspension cells that may be adapted to grow as adherent cells may also be used. In some embodiments, the anchorage-dependent cells used in the invention are Vero cells. It is within the knowledge of one skilled in the art to select an adherent host cell suitable for use in the process of the invention.

The virus may be any naturally occurring or genetically modified virus (e.g., recombinant or engineered virus). In certain embodiments, the virus is selected from a group consisting of naturally occurring or genetically modified VSV, adenovirus, Influenza virus, Ross River virus, Hepatitis A virus, Vaccinia virus, Herpes Simplex virus, Japanese Encephalitis virus, Herpes Simplex virus, West Nile virus, Yellow Fever virus, Rhino virus, Reovirus, Ebola-Zaire virus, Ebola-Sudan virus, Ebola-Marburg virus, Nipah virus, or chimeras of any of the foregoing. In some embodiments, the virus is a viral vector. In certain embodiments, the virus is a VSV vector. In certain embodiments, the virus is a modified viral vector, such as VSV, containing glycoprotein from another virus of interest.

In an embodiment of the invention, the virus is a virus vector. Viral vectors are viruses that may be used to transfer passenger nucleic acid sequences into a cell of interest. The viral vector may be a viral expression vector that may be used to derive recombinant proteins. Preferably, the viral vector may a modified Vaccinia virus Ankara (MVA), VSV, adeno-associated virus (AAV), lentivirus, retrovirus, adenovirus. More preferably, the viral vector of the invention is the VSV vector. The recombinant protein expressed by the viral vector may be a viral protein, a bacterial protein, a therapeutic recombinant protein, or a combination thereof. More preferably, the recombinant protein produced by the viral vector is a viral protein.

In some embodiments, the virus of the invention is a VSV vector. VSV, a member of the family Rhabdoviridae, is an enveloped virus with a negative-stranded RNA genome that causes a self-limiting disease in live-stock. Attenuated VSV are desirable viral vectors, as they are non-pathogenic in humans, almost non-virulent in animals, show robust growth in continuous mammalian cell lines of interest, lack a DNA intermediate during replication, elicit strong cellular and humoral immune response, and a genomic structure that allows insertion of transgenes at multiple sites (Humphreys and Sebastian, Immunology, 2018, 153:1-9; Clarke et al., Vaccine. 2016 34:6597-6609).

As used herein, "infection" or "virus infection" refers to the entry of a virus into the host cell and the subsequent replication of the virus in the cell. The infection of a host cell in the method of the disclosure may be carried out when the optimal window of infection as determined by the correlation of process air parameters, e.g., including Air flow, $O_2$ flow, and respective trends thereof resulting in increased virus yield.

The host cells of the method of the disclosure may be cultivated at an initial $dO_2$ of 100%. The $dO_2$ may be decreased to a level of 90% to a level as low as 20%, prior to infection. The $dO_2$ may be decreased from about 80% to about 60%, from about 70% to about 40%, from about 50% to about 15%. Preferably, the $dO_2$ may be decreased from about 50% to approximately 20%, before infection. More preferably, the level is decreased to about 20% before infection.

The $dO_2$ may be decreased starting at a time ranging from 2 to 24 hours prior to infection and kept at this level throughout the entire infection process and through the harvest of the virus. The $dO_2$ is decreased starting from about 2 hours to about 10 hours, from about 5 hours to about 15 hours, from about 10 hours to about 20 hours, and from 18 hours to about 24 hours before infection. Preferably the $dO_2$ is decreased starting at a time ranging from 8 hours to approximately 12 hours before infection.

"Harvesting" as used herein refers to the collection of cells and cell-derived products such as virus, by collecting unclarified culture media and/or host cells from the bioreactor. The harvesting of the virus, for example, may be performed 2 to 5 days post-infection, or 3 to 6 days post decrease of $dO_2$. In some embodiments, harvesting of the virus may be performed 2-days post infection. Some viruses may require an additional step of host cell lysis before harvest.

Viruses of the disclosure may be quantified by methods including but not limited to plaque assays, end-point dilution assays, hemagglutination assays, bicinchoninic acid assay, or electron microscopy. Preferably, the virus may be quantified by a plaque assay method. As used herein, a plaque assay method is a method to measure the number of infectious virus particles, based on its measurement of plaque-forming units (pfu). In the plaque assay, cell monolayers are infected with a serial dilution of the virus stock solution, and an agarose overlay is used to restrict the flow of virus. The infected cells release progeny virus, which in turn infect neighboring cells. The cells are lysed to produce clear regions surrounded by uninfected cells, called plaques, which are visualized using a dye. A higher sample virus titer leads to a higher number of plaques.

Embodiments of the subject invention provide novel and advantageous systems and methods for infecting host cells with a virus without a required step of counting the host cells. In one embodiment the system comprises a bioreactor configured and adapted for cell culture, infection of cells with a virus, propagation of the virus, and harvest of the virus; a cell culture media within the bioreactor; an air space above the cell culture media within the bioreactor; an air flow inlet into the bioreactor; an air flow sensor measuring air flow into the bioreactor; an $O_2$ flow inlet into the bioreactor; an $O_2$ flow sensor measuring $O_2$ flow into the bioreactor; a data collection module configured and adapted to collect the following values: current air flow into the bioreactor, current trend of air flow into the bioreactor, current $O_2$ flow into the bioreactor, and current trend of $O_2$ flow into the bioreactor; an indication unit configured and adapted to indicate when the following occur: a decreasing trend of air flow into the bioreactor, an increasing trend of $O_2$ flow into the bioreactor, and a convergence between the current respective values of air flow into the bioreactor and $O_2$ flow into the bioreactor.

In an embodiment, the data collection unit comprises: at least one first processor in operable communication with the air flow sensor and the $O_2$ flow sensor; and at least one first machine-readable medium in operable communication with the at least one first processor, the at least one first machine-readable medium having instructions stored thereon that, when executed by the at least one first processor, perform the following steps: recording a reading from the air flow sensor to produce a value of current air flow into the bioreactor, comparing the value of current air flow to at least one value of prior air flow to produce a current trend of air flow into the bioreactor, recording a reading from the $O_2$ flow sensor to produce a value of current $O_2$ flow into the bioreactor, and comparing the value of current $O_2$ flow to at least one value of prior $O_2$ flow to produce a current trend of $O_2$ flow into the bioreactor.

In an embodiment, the indication unit comprises: at least one second processor in operable communication with the data collection unit and the bioreactor; and at least one second machine-readable medium in operable communication with the at least one second processor, the at least one second machine-readable medium having instructions stored thereon that, when executed by the at least one second processor, perform the following steps: indicating a time window for infection of the cells with the virus if and only if: the current trend of air flow into the bioreactor is decreasing, the current trend of $O_2$ flow into the bioreactor is increasing, and a convergence exists between the current respective values of air flow into the bioreactor and $O_2$ flow into the bioreactor.

An increasing or decreasing trend may be defined by comparison of a single pair of data points (e.g., flow at a time TO versus flow at a time T1), by comparison of multiple data points (e.g., average of all flow values collected, observed, or recorded over a first time period versus average of all flow values collected, observed, or recorded over a second time period), or by other methods (e.g., statistical analysis, machine learning, or artificial intelligence methods). The criteria, methods, or thresholds for determining increasing or decreasing trend in one or more parameters may be the same or different.

Convergence is defined as a significant coming together of two values (e.g., air flow rate and $O_2$ flow rate) over time. Convergence may be calculated at a single point in time or at two nearby but discrete points in time by comparing a measurement of one flow rate against a measurement of another flow rate. The flow rates may be averaged, sampled, or otherwise processed before comparing. To determine or find a convergence, a convergence threshold may be set. The convergence threshold may be established in units of flow (e.g., mL/min) or on a percentage basis (e.g., the smaller value is within 30% of the larger value). Alternatively, flow values may be converted to a relative percentage and compared in percentage values (e.g., a flow threshold of +/−30% applied to a flow which is 62% air and 38% $O_2$ would have convergence). Alternatively, two values may be converted to an absolute percentage of the total flow and compared in percentage values (e.g., a flow threshold of +/−10% applied to a flow which is 42% air, 12% N2, and 46% $O_2$ would have convergence between airflow and $O_2$ flow).

Embodiments may further comprise a decision making unit configured and adapted to initiate infection of the cells with the virus when the time window for infection of the cells with the virus is indicated. Each of the data collection unit, indicating unit, and decision making unit (taken individually or in any combination) may be, comprise, include, or be connected to any of a digital computer, an embedded part of a controller (e.g., a module or application within a commercial or fabricated bioreactor control unit), a mechanical system, a pneumatic or hydraulic system, an analog electrical or electronic system, a standard operating procedure, a person, or a combination of any of the preceding.

In an embodiment, the at least one first processor and the at least one second processor are the same processor.

In an embodiment, the at least one first machine-readable medium and the at least one second machine-readable medium are the same machine-readable medium.

In an embodiment, the bioreactor is a sealed bioreactor.

In an embodiment, a convergence threshold is selected as +/−20% and convergence is found when the value of percent $O_2$ flow into the bioreactor is within +/−20% of the value of percent air flow into the bioreactor.

In an embodiment, the data collection module comprises mechanical or analog electrical sensors.

In an embodiment, the indication unit comprises one or more audible, visual, or tactile indicators.

An embodiment provides a method for infecting host cells with a virus without a required step of counting the host cells. The method may comprise: providing a bioreactor configured and adapted for cell culture, infection of cells with a virus, propagation of the virus, and harvest of the virus; providing a cell culture media within the bioreactor; providing an air space above the cell culture media within the bioreactor; providing an air flow inlet into the bioreactor; providing an air flow sensor measuring air flow into the bioreactor; providing an $O_2$ flow inlet into the bioreactor; providing an $O_2$ flow sensor measuring $O_2$ flow into the bioreactor; collecting, by a data collection module, the following: current air flow into the bioreactor, current trend of air flow into the bioreactor, current $O_2$ flow into the bioreactor, and current trend of $O_2$ flow into the bioreactor; indicating, by an indication unit, when the following occur: a decreasing trend of air flow into the bioreactor, an increasing trend of $O_2$ flow into the bioreactor, and a convergence between the current respective values of air flow into the bioreactor and $O_2$ flow into the bioreactor.

In an embodiment, the data collection unit comprises: at least one first processor in operable communication with the air flow sensor and the $O_2$ flow sensor; and at least one first machine-readable medium in operable communication with the at least one first processor, the at least one first machine-readable medium having instructions stored thereon that, when executed by the at least one first processor, perform the following steps: recording a reading from the air flow sensor to produce a value of current air flow into the bioreactor, comparing the value of current air flow to at least one value of prior air flow to produce a current trend of air flow into the bioreactor, recording a reading from the $O_2$ flow sensor to produce a value of current $O_2$ flow into the bioreactor, and comparing the value of current $O_2$ flow to at least one value of prior $O_2$ flow to produce a current trend of $O_2$ flow into the bioreactor.

In an embodiment, the indication unit comprises: at least one second processor in operable communication with the data collection unit and the bioreactor; and at least one second machine-readable medium in operable communication with the at least one second processor, the at least one second machine-readable medium having instructions stored thereon that, when executed by the at least one second processor, perform the following steps: indicating a time window for infection of the cells with the virus if and only if: the current trend of air flow into the bioreactor is decreasing, the current trend of $O_2$ flow into the bioreactor is increasing, and a convergence exists between the current respective values of air flow into the bioreactor and $O_2$ flow into the bioreactor.

In an embodiment, the method may further comprise initiating infection of the cells with the virus when the time window for infection of the cells with the virus is indicated.

In an embodiment, the at least one first processor and the at least one second processor are the same processor.

In an embodiment, the at least one first machine-readable medium and the at least one second machine-readable medium are the same machine-readable medium.

In an embodiment, the bioreactor is a sealed bioreactor.

In an embodiment, the value of $O_2$ flow into the bioreactor is within +/−20% of the value of air flow into the bioreactor.

In an embodiment, the data collection module comprises mechanical or analog electrical sensors.

In an embodiment, the indication unit comprises one or more audible, visual, or tactile indicators.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium. It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

All patents, patent applications, provisional applications, and publications referred to or cited herein are incorporated by reference in their entirety, including all figures and tables, to the extent they are not inconsistent with the explicit teachings of this specification.

Materials and Methods

The iCELLis Nano fixed-bed bioreactor system was used in Examples 1-4. The iCELLis Nano bioreactor can hold about 800 mL, which is equivalent to about 5,300 to 40,000 total surface growth area with a fixed-bed height of 20 mm to 10 mm. The growth area was equivalent to 35 to 267 T-150 flasks that could be used for stacked growth (see FIG. 5A, 5B, and Table 1). Runs with different parameters were performed with the iCELLis.

The scale-X™ Carbo fixed-bed bioreactor system of Univercells may be used in Prophetic Examples 5-7 (Berrie D M et al.; *Vaccine*, 2020, 38: 3639-3645). The scale-X™ Carbo bioreactor has a surface area for cell growth in the range of 10 $m^2$-30 $m^2$ in a total vessel volume of 1.6-3.2 L, dependent on the surface area. Runs with different parameters may be performed with the scale-X™ Carbo bioreactor.

Following are examples that illustrate procedures for practicing the invention. These examples should not be construed as limiting. All percentages are by weight and all solvent mixture proportions are by volume unless otherwise noted.

Example 1. VSV Production from a Campaign where the Parameters Served as a Baseline for Virus Production Vero cells were grown at approximately 100% dOi, 37° C. temperature, 7.4 pH in iCELLis bioreactor. Over the cultivation period of the Vero cells, the biomass sensor of the bioreactor was used to monitor cell growth, and the Vero cells were infected with VSV at 55 mS/cm conductivity (a measure of cell growth). rVSV-LASV was provided by NIAID under Material Transfer Agreement LAB-18-P_LV-22.

The system reached the highest conductivity (highest cell growth) of about 75 mS/cm about 12-24 hours after infection. The infection was at 0.05 MOI. The virus was harvested 2 days post-infection. Virus production was increased in excess of 1 log per mL when compared to titers from the same cells growing in flat-stock (Table 2).

Example 2. VSV Production from a Campaign where the $dO_2$ was Decreased for Approximately 12 Hours Prior to Infection and Maintained Through Infection to Harvest Vero cells were cultivated at approximately 100% $dO_2$, 37° C. temperature, 7.4 pH. Over the cultivation period of the Vero cells, the biomass sensor was used to monitor cell growth, and the cells were infected at 80 mS/cm conductivity (approximately highest conductivity), i.e., the Vero cells were infected when maximum cell growth was reached.

Approximately 12 hours before infection the $dO_2$ level was lowered to 45-50% and kept constant at this decreased level throughout infection and through harvest. The temperature was maintained at 37° C., and pH was maintained at 7.4. The virus was harvested approximately 2 days after infection. Decreasing the $dO_2$ 12 hours prior to infection, infecting Vero cells VSV after the Vero cells achieved maximum cell growth, resulted in a VSV titer increase of over 2 logs when compared to VSV titer from flat-stock (Table 2) and a 5.9× increase in viral titer when compared to that of Example 1 (no $dO_2$ decrease). rVSV-LASV was provided by NIAID under Material Transfer Agreement LAB-18-P_LV-22.

Example 3. VSV Production from a Campaign with Maximum Conductivity in Addition to the $dO_2$, pH, and Temperature Remaining Constant Vero cells were cultivated at approximately 100% $dO_2$, 37° C. temperature, 7.4 pH in the bioreactor. Over the cultivation period of the Vero cells, the biomass sensor was used to monitor cell growth, and the cells were infected at 110 mS/cm conductivity (approximately highest conductivity, and therefore when maximum cell growth was reached). The infection was at 0.05 MOI. No adjustment was made to the $dO_2$ levels. The temperature was maintained at 37° C., and pH was maintained at 7.4 throughout the cultivation and infection period. The virus was harvested approximately 2 days post infection. The VSV titer from this experiment was similar to that of Example 1, showing that the higher yield observed in Example 2 was due the modification of the $dO_2$ and not due to infecting the Vero cells at highest cell growth, which could presumably increase the overall titer to due to more cells becoming infected (Table 2).

TABLE 2

Viral Titers from Bioreactor Production

|  | CS10 Flatstock | Run 1 | Run 2 | Run 3 |
| --- | --- | --- | --- | --- |
| $0_2$% during Infection | NA | 90% | 40% | 20% |
| Titer (pfu/mL) | 1.30E+06 | 8.49E+06 | 9.17E+07 | 1.13E+08 |
| Total Virus Production (pfu) | 1.30E+09 | 6.79E+09 | 7.33E+10 | 9.07E+10 |

Table 2 compares the propagation data between different runs. The propagation data was compared between: 1. VSV propagated from Vero cells in a flat-stock flask, 2. VSV propagated from Vero cells in an iCELLis system (Run 1), where $dO_2$% during infection is 90%, 3. VSV propagated from Vero cells in an iCELLis system (Run 2) where $dO_2$% during infection is 40%, and 4. VSV propagated from Vero cells in an iCELLis system (Run 3) where $dO_2$% during infection is 20%. The data in Table 2 shows a significant increase in VSV titer, and total virus production progressively, from CS10 flask-stock, Run 1, Run 2, and Run 3, respectively. This shows that using the flat-bed bioreactor iCELLis to propagate VSV resulted in a 1 to 2 log increase in virus production per mL when compared to virus produced from flat-stock. More significantly, a progressive decrease in $dO_2$ during infection resulted in a progressively significant increase in VSV titer and total virus production. rVSV-LASV was provided by NIAID under Material Transfer Agreement LAB-18-P_LV-22.

Example 4. VSV Production at Different $dO_2$ Levels at Infection

VSV was grown in Vero cells at approximately 100% $dO_2$, 37° C. temperature, 7.4 pH. Approximately 12 hours before infection the $dO_2$ level was lowered to 90%, 40%, and 20% and kept constant at this decreased level throughout infection. The temperature was maintained at 37° C., and pH was maintained at 7.4. The virus was harvested approximately 2 days after infection. The results, as shown in Table 2, show a progressive increase in virus yield with the level of $dO_2$ decrease at infection. rVSV-LASV was provided by NIAID under Material Transfer Agreement LAB-18-P_LV-22.

Prophetic Example 5—VSV Production from a Campaign where the Parameters May Serve as a Baseline for Future Virus Production Vero cells may be grown at approximately 100% $dO_2$, 37° C. temperature, 7.4 pH in Univercells scale-X™ Carbo Bioreactor, using a suitable chemically defined serum free media. Over the cultivation period of the Vero cells, the $O_2$ and airflow sensors may be used to monitor process air parameters, and the Vero cells may be infected with VSV upon observance of a decreasing trend of total air flow into the bioreactor, an increasing trend of total $O_2$ flow into the bioreactor, and a convergence (e.g., +/−20%) of the current respective values of total air flow into the bioreactor and total $O_2$ flow into the bioreactor (an indicator of metabolically active cell density). The virus may then be harvested 2 to 5 days post-infection. Virus production could be expected to increase in excess of 1 log per mL when compared to titers from the same cells growing in flat-stock (similar to actual results shown in Table 2).

Prophetic Example 6—Influenza Production from a Campaign where the Parameters May Serve as a Baseline for Future Virus Production Quail cells may be grown at approximately 100% $dO_2$, 37° C. temperature, 7.4 pH in Univercells scale-X™ Carbo Bioreactor, using a suitable chemically defined serum free media. Over the cultivation period of the Quail cells, the $O_2$ and airflow sensors may be used to monitor process air parameters, and the Quail cells may be infected with VSV upon observance of a decreasing trend of total air flow into the bioreactor, an increasing trend of total $O_2$ flow into the bioreactor, and a convergence (e.g., of the current respective values of total air flow into the bioreactor and total $O_2$ flow into the bioreactor (an indicator of metabolically active cell density). The virus may then be harvested 2 to 5 days post-infection. Virus production could be expected to increase in excess of 1 log per mL when compared to titers from the same cells growing in flat-stock (similar to actual results shown in Table 2).

Prophetic Example 7—LVV Production from a Campaign where the Parameters May Serve as a Baseline for Future Virus Production HEK 293 cells may be grown at approximately 100% $dO_2$, 37° C. temperature, 7.4 pH in Univercells scale-X™ Carbo Bioreactor, using a suitable chemically defined serum free media. Over the cultivation period of the HEK 293 cells, the $O_2$ and airflow sensors may be used to monitor process air parameters, and the HEK 293 cells may be infected with VSV upon observance of a decreasing trend of total air flow into the bioreactor, an increasing trend of total $O_2$ flow into the bioreactor, and a convergence (e.g., of the current respective values of total air flow into the bioreactor and total $O_2$ flow into the bioreactor (an indicator of metabolically active cell density). The virus may then be harvested 2 to 5 days post-infection. Virus production could be expected to increase in excess of 1 log per mL when compared to titers from the same cells growing in flat-stock (similar to actual results shown in Table 2).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of producing virus in a bioreactor comprising the following steps:
    a) providing host cells in the bioreactor;
    b) growing the host cells in the bioreactor under a set of bioreactor process air parameters comprising an air mass flow rate and an oxygen mass flowrate;
    c) reducing the air mass flow rate and increasing the oxygen mass flow rate;
    d) infecting the host cells with at least one virus or virus particle after the lower flow rate of the air mass flow rate or the oxygen mass flow rate is within ±30% of the larger flow rate of the air mass flow rate or the oxygen mass flow rate;
    e) incubating the host cells infected with the virus or virus particle to propagate the virus or virus particle; and
    f) harvesting the virus or virus particle.

2. The method of claim 1, wherein the host cells are adherent cells.

3. The method of claim 2, wherein the bioreactor is a flat-bed bioreactor, and the step of growing the host cells is at a constant initial $dO_2$ level, pH, and temperature.

4. The method of claim 1, wherein infecting the host cells in d) comprises infecting the host cells when the air mass flow rate and the oxygen mass flow rate into the bioreactor are equal.

5. The method of claim 1, wherein infecting the host cells in d) comprises infecting the host cells when the air mass flow rate and the oxygen mass flowrate into the bioreactor are within ±20% of each other, or within ±10% of each other, or within ±5% of each other.

6. The method of claim 1, wherein the infecting the host cells in d) occurs at a multiplicity of infection (MOI) of 0.1 to 0.05.

7. The method of claim 6, wherein the step of incubating of e) comprises incubating the host cells at a second dissolved oxygen ($dO_2$) level, pH, and temperature different from a first $dO_2$ level, pH, and temperature during the growing the host cells of b).

8. The method of claim 1, wherein the host cells are Vero cells, MBCK cells, MDBK cells, MRC-5 cells, BSC-1 cells, LLC-MK cells, CV-1 cells, CHO cells, COS cells, HeLa cells, HEK 293 cells, MDOK cells, CRFK cells, RAF cells, TCMK cells, LLC-PK cells, PK 15 cells, Wl-38 cells, T-FLY cells, BHK cells, SP2/0 cells, NS0 cells, PerC6 cells, COR cells, or QOR cells.

9. The method of claim 1, wherein the host cells are Vero cells.

10. The method of claim 1, wherein the virus is selected from among naturally occurring or genetically modified VSV, adenovirus, Influenza virus, Ross River virus, Hepatitis A virus, Vaccinia virus, Herpes Simplex virus, Japanese Encephalitis virus, Herpes Simplex virus, West Nile virus, Yellow Fever virus, Rhino virus, Reovirus, Ebola-Zaire virus, Ebola-Sudan virus, Ebola-Marburg virus, Nipah virus, or chimeras of any of the foregoing.

11. The method of claim 1, wherein the virus or virus particle is a viral vector.

12. The method of claim 1, wherein the virus or virus particle is a modified viral vector, containing glycoprotein from another virus of interest.

13. The method of claim 1, the bioreactor has a capacity of at least 600 $m^2$.

14. The method of claim 1, wherein the host cells in the bioreactor are not counted prior to said infecting, or are not counted prior to said harvesting.

15. The method of claim 1, wherein the bioreactor is a sealed system.

16. The method of claim 1, further comprising the step of determining a virus titer by a plaque assay method.

17. The method of claim 16, further comprising the step of purifying and or characterizing of the virus or virus particle.

18. The method of claim 1, further comprising the step of producing a vaccine with the virus or virus particle.

19. The method of claim 1, wherein the bioreactor includes chemically defined media.

20. The method of claim 1, wherein the harvesting the virus or virus particle of f) occurs 2 to 5 days after the infecting of d).

21. The method of claim 1, further comprising decreasing a first oxygen dissolved oxygen ($dO_2$) level to a second $dO_2$ level in the bioreactor 2 to 24 hours prior to the infecting of d).

22. The method of claim 21, wherein the first $dO_2$ level is 100%, and wherein the second $dO_2$ level is between 50% to 20%.

23. The method of claim 21, wherein the harvesting the virus or virus particle of f) occurs 3 to 6 days after decreasing the first $dO_2$ level in the bioreactor.

24. The method of claim 1, wherein the reducing the air mass flow rate and increasing the oxygen mass flow rate of c) increases a maximum number of viable host cells, wherein the maximum number of viable host cells is reached when the lower flow rate of the air mass flow rate or the oxygen mass flow rate is within ±30% of the larger flow rate of the air mass flow rate or the oxygen mass flow rate, wherein the infecting of d) occurs when there are a maximum number of viable host cells in the bioreactor.

* * * * *